(12) United States Patent
Huckfeldt et al.

(10) Patent No.: US 9,387,142 B2
(45) Date of Patent: Jul. 12, 2016

(54) SANITARY DISPOSABLE UNISEX URINE DEVICE

(71) Applicant: Mercy Medical Research Institute, Springfield, MO (US)

(72) Inventors: Roger Huckfeldt, Nixa, MO (US); Cindy Lowe, Nixa, MO (US); Keela Davis, Springfield, MO (US); Martin Reuter, Flemington, MO (US); John Price, Springfield, MO (US); Debbie Sue Mikkelson, Willard, MO (US)

(73) Assignee: Mercy Medical Research Institute, Springfield, MO (US)

( * ) Notice: Subject to any disclaimer, the term of this patent is extended or adjusted under 35 U.S.C. 154(b) by 0 days.

(21) Appl. No.: 14/500,320

(22) Filed: Sep. 29, 2014

(65) Prior Publication Data
US 2015/0018793 A1    Jan. 15, 2015

Related U.S. Application Data

(63) Continuation of application No. 13/495,691, filed on Jun. 13, 2012, now Pat. No. 8,847,001.

(60) Provisional application No. 61/496,307, filed on Jun. 13, 2011.

(51) Int. Cl.
| | |
|---|---|
| *A61F 5/451* | (2006.01) |
| *A61F 5/455* | (2006.01) |
| *A61F 5/453* | (2006.01) |
| *A61G 9/00* | (2006.01) |
| *A61B 10/00* | (2006.01) |

(52) U.S. Cl.
CPC .............. *A61G 9/006* (2013.01); *A61F 5/4556* (2013.01); *A61B 10/007* (2013.01); *A61G 2200/12* (2013.01)

(58) Field of Classification Search
CPC ... A61F 5/4556; A61G 2200/12; A61G 9/006
See application file for complete search history.

(56) References Cited

U.S. PATENT DOCUMENTS

| | | | | |
|---|---|---|---|---|
| 2,358,850 | A * | 9/1944 | Chenault ................ | A61G 9/006 222/538 |
| 4,771,484 | A * | 9/1988 | Mozell ................. | A61F 5/4556 4/144.4 |
| 4,816,027 | A * | 3/1989 | Gilchrist ................ | A61F 5/445 604/332 |
| 5,392,941 | A * | 2/1995 | Robbins, III ....... | A47G 23/0241 220/666 |
| 5,690,622 | A * | 11/1997 | Smith et al. .................... | 604/333 |
| 5,745,926 | A * | 5/1998 | Cailleteau ................ | A61F 5/44 383/44 |
| 5,946,738 | A * | 9/1999 | Cailleteau ............. | A61F 5/4404 4/144.1 |

(Continued)

*Primary Examiner* — Susan Su
(74) *Attorney, Agent, or Firm* — Michael A. Williamson; Polsinelli PC (57) ABSTRACT

A sanitary disposable urine device is provided. The device includes an inner ring and outer ring each having a top surface and opposing bottom surface. The outer ring is substantially concentric with the inner ring and may be offset. At least one of the top surfaces of the inner and outer rings conforms to a body contour of a user's perineum. The device further includes a hand holder coupled to the bottom surface of the inner ring, the hand holder having an opening configured to match to the inner ring. The device also includes a fluid containing bag having an open end attached to the hand holder such that fluid flows through the inner ring and the opening of the hand holder into the fluid containing bag during usage. The device also includes an inner bag inside the fluid containing bag for containing an absorbent material and an outer sealable bag to secure the device after use.

7 Claims, 11 Drawing Sheets

(56) References Cited

U.S. PATENT DOCUMENTS

| | | | | |
|---|---|---|---|---|
| 6,543,064 B1* | 4/2003 | Prall | A61G 9/006 | 4/144.1 |
| 7,998,126 B1* | 8/2011 | Fernandez | A61F 5/4556 | 604/319 |
| 8,211,072 B2* | 7/2012 | Smith | A61F 5/448 | 156/254 |
| 8,388,587 B1* | 3/2013 | Gmuer | A61F 5/4556 | 604/347 |
| 2002/0193762 A1* | 12/2002 | Suydam | A61F 5/4556 | 604/327 |
| 2004/0059306 A1* | 3/2004 | Tsal | A61F 5/4404 | 604/332 |
| 2004/0064112 A1* | 4/2004 | Sun | A61G 9/006 | 604/346 |
| 2005/0070864 A1* | 3/2005 | Fellion | A61F 5/4407 | 604/346 |
| 2006/0041236 A1* | 2/2006 | Qian | A61G 9/006 | 604/322 |
| 2008/0004580 A1* | 1/2008 | Mullejans | A61F 5/441 | 604/344 |
| 2009/0216208 A1* | 8/2009 | Leisner | A61F 5/448 | 604/344 |
| 2010/0094233 A1* | 4/2010 | Ashworth | | 604/317 |
| 2011/0087183 A1* | 4/2011 | Yang | A61F 5/4408 | 604/347 |
| 2012/0222208 A1* | 9/2012 | Jacobson | A61F 5/4556 | 4/484 |

* cited by examiner

SANITARY DISPOSABLE UNISEX URINE DEVICE

RELATED APPLICATIONS

This application is a continuation of U.S. patent application Ser. No. 13/495,691, filed Jun. 13, 2012 which claims benefit of U.S. patent application Ser. No. 61/496,307 filed Jun. 13, 2011, the disclosure of which is incorporated herein by reference.

BACKGROUND OF THE INVENTION

This disclosure relates to a receptacle for waste, particularly a disposable urine collection device that allows users to urinate with minimal spill. In particular, the disposable urine devices are useful for bed ridden patients in hospitals or similar settings.

A number of issued and pending patents exist for urinal devices. These urinal devices vary in configuration and construction from rigid plastic devices to flexible devices intended for use in non-hospital settings. Most of the urinal devices relate to ease of use and retention of liquids. The devices are generally divided into two general categories, one category intended to receive urine from patients having an indwelling catheter and the second category for use with patient not having catheters.

A number of patents disclose the use of flexible urinal bags. Absorbent materials are sometimes used within the urinal bags to absorb and retain urine to prevent leaks and spills. The urinal bags are formed to accommodate both male and female users. U.S. Pat. No. 5,885,262 to Wheeler, U.S. Pat. No. 5,354,132 and U.S. Pat. No. 5,318,549 to Yang described various devices to utilize plastic bags having absorbent materials disposed therein to receive and retain bodily liquids. These devices differ in their constructions and use from the inventive devices described herein.

Several patents relate more specifically to the receptacle portion of urine bags with the intent of providing a comfortable and leak proof seal between the urinal bag and the perineum of a female user. For example, U.S. Pat. No. 5,370,637 to Brodeur, U.S. Pat. No. 684414 to Rehrig, U.S. Pat. No. 6,070,277 to Thomas, U.S. Pat. No. 6,796,974 to Palumbo, and U.S. Pat. No. 6,668,388 to Buttigieg, all relate to a funnel or collecting receiver that during use is positioned against the perineum of the user during urination. None of these devices allow a comfortable fitment of the device to the patient, lead free use and easy disposal.

A commercial device under the trade name "TravelJohn" is substantially disclosed and described in U.S. patent application Ser. No. 2002/0193762 to Suydam. The TravelJohn device includes an inner plastic sleeve mounted in an outer bag that is closable. At the open end of the inner sleeve, a unisex plastic adapter is attached. The outer bag includes absorbent material to receive and retain urine. The plastic adapter is configured to fit snuggly against the perineum of a female user. Male users simply urinate through the opening provided in the plastic adapter. Urine would likely be spilled during use of the TravelJohn device if a gap is maintained between the device and the user.

There still remains a need for a urine catching device for patients who need assistance to urinate that is comfortable, easy to use and can be disposed with minimal contact between medical personal and the patient's urine. It is highly desirable to minimize urine spill during usage of urine catching device. The device needs to be configured for use with a bed-ridden patient that is not able to provide any assistance to medical personnel when they urinate. The inventive device will be particularly useful with obese patients that cannot be lifted and placed on traditional bedpans.

BRIEF SUMMARY

This disclosure advances the art and overcomes the problems outlined above by providing disposable unisex urine devices that minimize urine spill both during use, shipping after use and during disposal and provide comfort for both male and female users. The device eliminates the need to empty the urinal after use and the device can be disposed as medical waste with the urine sealed within the device.

In one embodiment, a sanitary disposable unisex urine device is provided. The sanitary disposable unisex urine device includes an inner ring having a top surface and opposing bottom surface. The device also includes an outer ring having a top surface, the outer ring being substantially concentric with the inner ring. At least one of the top surfaces of the inner and outer rings conforms to a body contour of a female user. The device further includes a hand holder coupled to the bottom surface of the inner ring, the hand holder having an opening configured to match to the inner ring. The device also includes a fluid containing bag having an open end attached to an outer surface of the hand holder such that fluid flows through the inner ring and the opening of the hand holder into the fluid containing bag during usage. In one embodiment, an inner bag is inside the fluid containing bag and contains an absorbent material which captures fluids to minimize the quantity of free-flowing fluid within the bag.

In another embodiment, the device further includes an outer shield bag attached to the outer surface of the hand holder at a position closer to the bottom surface of the inner ring than the fluid containing bag. The outer shield bag is also provided with a liquid tight closure that allows the fluid containing bag, hand holder and absorbent rings to be fully encapsulated and closed for transport and disposal.

In a specific embodiment, the hand holder may include an angled portion for directing flow of fluid. The fluid containing bag has an angled side that matches the angled portion of the hand holder. The hand holder may also include a non-angled portion coupled to the angled portion, the angled portion being closer to the inner ring than the non-angled portion.

In an alternative embodiment, the outer ring has a different lateral length from the inner ring to accommodate lateral offset of the rings which allows better fitment of the absorbent rings to the body of the person urinating into the device.

In an embodiment, a method of utilizing a disposable unisex urine device by a user is provided. The urine device includes two substantially concentric rings that conform to a body contour of a female user, an angled hand holder coupled to the rings, a fluid containing bag coupled to the hand holder, and an outer shield bag coupled to the hand holder. The method includes positioning the urine device, flowing the urine through the rings and an opening of the hand holder into the fluid containing bag of the urine device, and reversing the outer shield bag to seal the fluid containing bag of the urine device. The method also includes reversing the outer shield bag to seal the fluid containing bag and the rings of the urine device and transporting the urine device for disposal of the urine.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings.

DETAILED DESCRIPTION

The present disclosure may be understood by reference to the following detailed description taken in conjunction with the drawings as briefly described below. It is noted that, for purposes of illustrative clarity, certain elements in the drawings may not be drawn to scale.

The disclosure provides a disposable bag with at least two concentric rings mounted at an opening of a disposable bag. The rings are manufactured from absorbent materials. The inner and outer rings provide an absorbent area for contacting the body of the person urinating into the device to increase comfort, to decrease the splashing of urine during use and to minimize leakage between the bag and user. The disposable bag also includes an outer shield bag, which covers and protects the hand of the user or assistant during use and which includes a closure to prevent the spill of urine during transport of the bag.

Figure 1A:
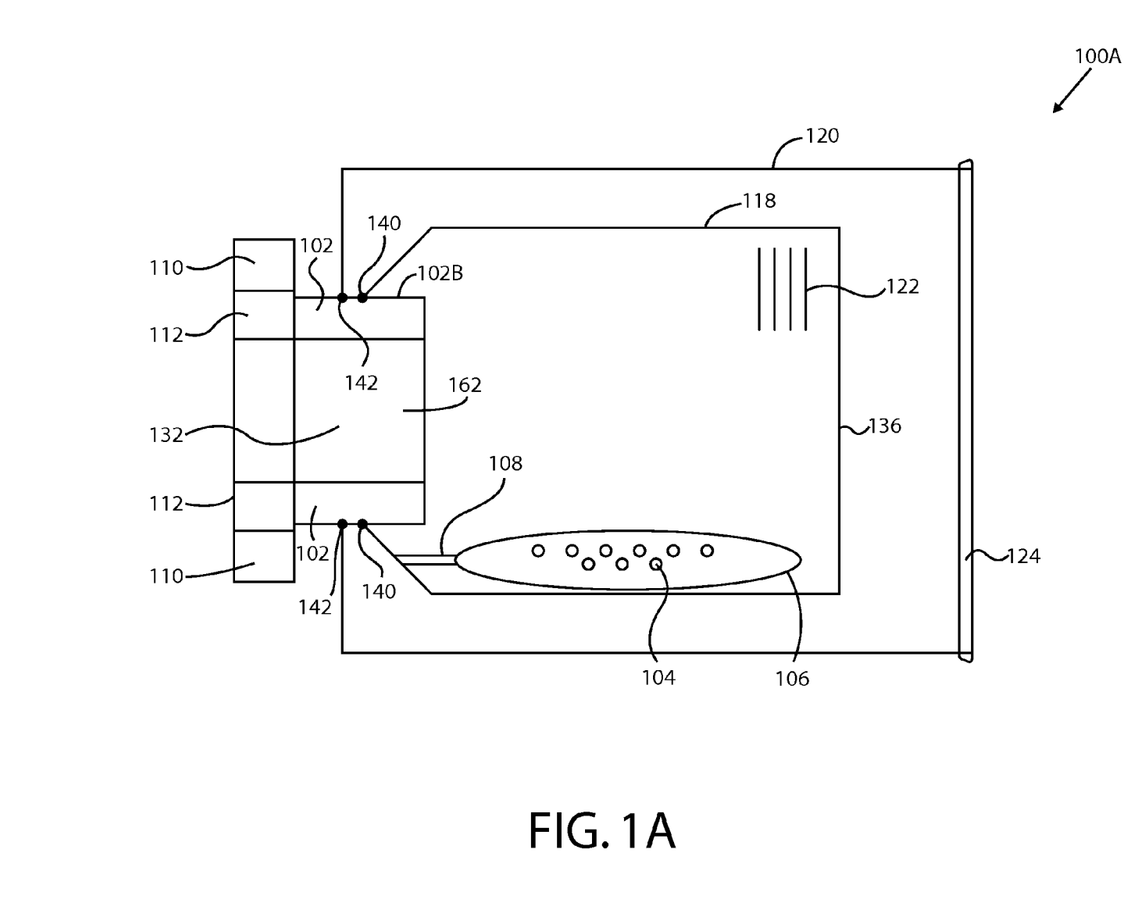
FIG. 1A is a simplified diagram illustrating a disposable urine catching device in one embodiment.

FIG. 1A is a simplified diagram illustrating a disposable urine catching device 100A in an embodiment. Device 100A includes a urine containment bag 118 having an open end 132 and a closed end 136. Device 100A also includes an inner bag 106 containing absorbent powders 104 positioned inside urine containment bag 118. Inner bag 106 is attached to urine containment bag 118 through an attachment mechanism 108. Inner bag 106 may also be coupled to hand holder 102 to improve urine contact area to speed urine absorbance (see FIG. 1D).

Device 100A also includes an inner ring 112 and an outer ring 110 near open end 132 of urine containment bag 118. An outer ring 110 is substantially concentric with inner ring 112. Outer ring 110 and inner ring 112 provide means to accommodate different body contours and fit to the perineum of a female user to ensure comfortable seal and contact. Both inner ring 112 and outer ring 110 may have an identical lateral length, or may have a different lateral length (see FIGS. 5A-5B) to form an offset between the two rings. The inner and outer rings may be initially substantially elliptically shaped. The initial shapes of the rings may be changed to shapes that are more circular.

The inner ring 112 is coupled to a hand holder 102. Hand holder 102 has an opening which may be initially substantially elliptically shaped. Hand holder 102 provides a firm support for a user to grasp onto but is also flexible enough to allow the user to manipulate its shape. Because hand holder 102 is coupled to the bottom of inner ring 112 and outer ring 110, the shapes of inner ring 112 and outer ring 110 are changed as a result of shape change of hand holder 102. The resultant shape of the inner and outer rings help improve the seal between the perineum and the inner and outer rings. This shape change of the hand holder is accomplished by squeezing the hand holder 102 with fingers, which alters the shape of the opening from its initial elliptical configuration to a more circular opening. Near open end 132 of urine containment bag 118, urine containment bag 118 attaches to an outer surface 102B of hand holder 102 at location 140.

Device 100A further includes an outer shield bag 120 that is attached to outer surface 102B of hand holder 102 at location 142, which is closer to inner ring 112 than location 140 at which urine containment bag 118 attaches to outer surface 102B of hand holder 102. Outer shield bag 120 may be longer (as shown in FIG. 1A) or shorter (not shown) than urine containment bag. Outer shield bag 120 has a sealable closure 124 such that when outer shield bag 120 is reversed, both inner ring 112 and outer ring 110 are sealed inside outer shield bag 120 by sealable closure 124, such as Ziploc®. Ziploc® is a brand of reusable, re-sealable zipper storage bags and containers originally developed by Dow Chemical Company, and now produced by S. C. Johnson & Son.

Urine containment bag 118 is used to contain urine while allowing visibility to read the measurements of excretion of urine in urine containment bag 118. Urine containment bag 118 may be made of any clear plastic film or colored plastic film, for example, polyethylene film. Visible reading measurements 122 near closed end 136 of urine containment bag 118 may range, for example, from 100 ml to 700 ml with increments of 100 ml.

Figure 1B:
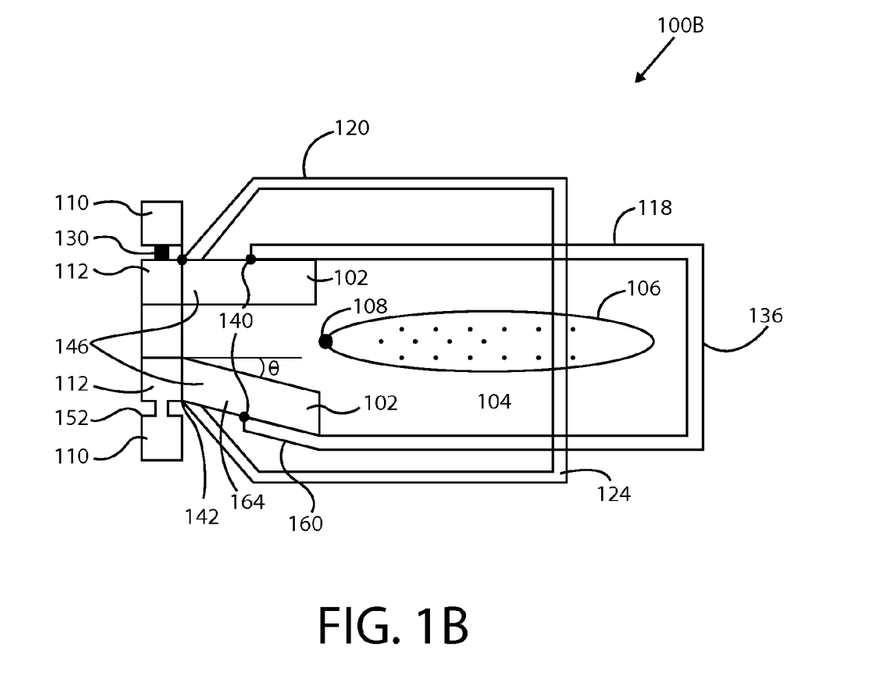
FIG. 1B is a simplified diagram illustrating a disposable urine catching device in another embodiment.

FIG. 1B is a simplified diagram illustrating a disposable urine catching device 100B in another embodiment. Note that hand holder 102 has a different shape from that shown in FIG. 1A.

Figure 1C:
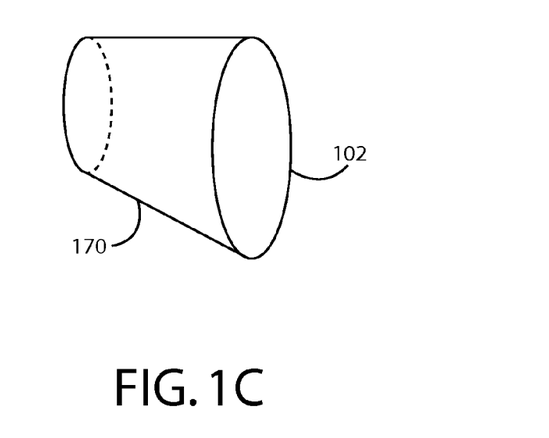
FIG. 1C is a perspective view of hand holder of FIG. 1B.

FIG. 1C is a perspective view of angled hand holder 102 of FIG. 1B. As illustrated in FIGS. 1B-C, hand holder 102 has an angled side on the bottom to provide structural support for angled side 160 of urine containment bag 118. Device 100B also has attachment 142 of outer shield bag to hand holder 102 near the joint 146 between inner ring 112 and hand holder 102. Device 100B also has the outer shield bag 120 shorter than urine containment bag 118. Outer shield bag 120 may also be longer than urine containment bag 118 (not shown). Device 100B has an attachment 108 for inner bag 106 in the middle of urine containment bag 118. Inner bag 106 may also be attached to hand holder 102 (not shown). It will be appreciated by those skilled in the art that device 100B may vary position of attachment 108 (see FIGS. 2A-2C for more embodiments).

Figure 1D:
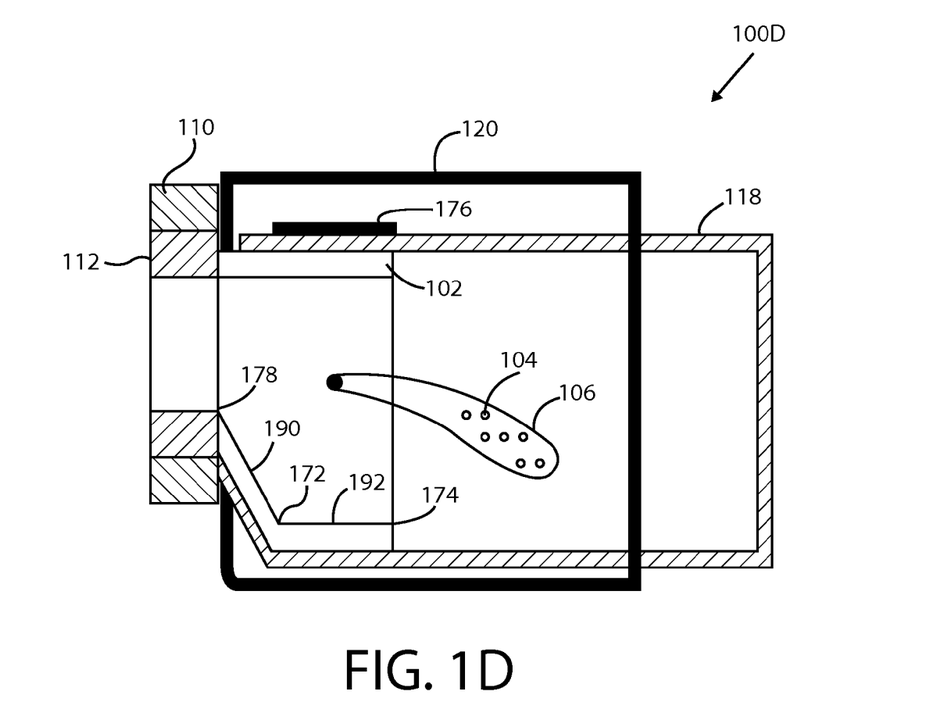
FIG. 1D is a simplified diagram illustrating a disposable urine catching device in a further embodiment.

FIG. 1D illustrates a side view of urine disposable device 100D in another embodiment. Hand holder 102 in FIG. 1D has a different shape from hand holders 102A and 102B in FIGS. 1A and 1B. Hand holder 102 includes an angled portion 190 between locations 178 and 172 and a non-angled portion 192 between points 172 and 174. The angled portion helps direct urine flow into the urine containment bag 118. Urine disposable device 100D includes a circumferential layer 176 applied around non-angled portion of hand holder 102 between points 172 and 174, and is used to reinforce the bonding of urine containment bag 118 to hand holder 102. The circumferential layer 176 may be made of polyethylene foam tape with acrylic adhesive on one side, such that circumferential layer 176 bonds to the urine containment bag 118 that covers hand holder 102. Inner bag 106 may be attached to hand holder 102 or the portion of urine containment bag 118 that covers hand holder 102. The circumferential layer 176 may also help reinforce the bonding between inner bag 106 and hand holder 102 or urine containment bag 118.

Figure 1E:
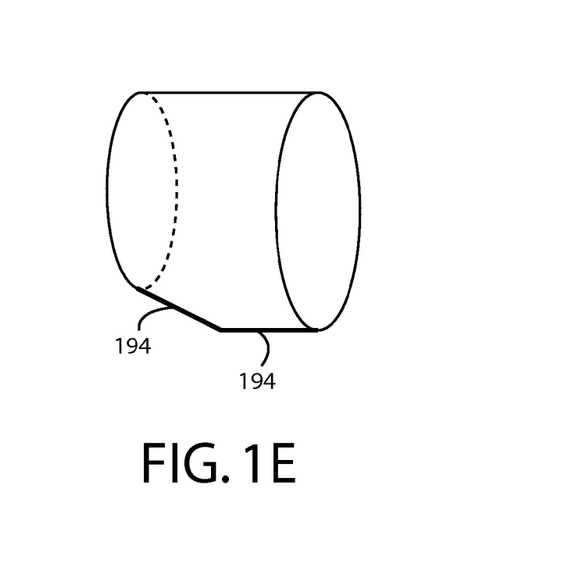
FIG. 1E is a perspective view of hand holder of FIG. 1D.

FIG. 1E is a perspective view of angled hand holder, or tube, 102 of FIG. 1D. Angled portion 190 of hand holder 102 is coupled to non-angled portion 192. As can be seen in FIG. 1E, angled portion 190 comprises the open-ended frustrum of a symmetric or asymmetric cone and non-angled portion 192 comprises an elliptic or circular cylinder, the non-angled portion 192 extending from the larger base of the frustrum of the angled portion. The smaller base of the frustrum 190 comprises the first end of tube 102. Hand holder 102 may be formed from a sheet material with a seam 194 along the angled portion and the non-angled portion or molded in one piece. If the seam 194 is present, an adhesive tape 176 may be used to reinforce the seam. If the hand holder is molded in one piece, the seam is not present such that adhesive tape 176 is not needed. Hand holder 102 has an initial substantially elliptical shape. When squeezed by a user, the hand holder 102 may change its opening from an initial substantially elliptical shape to a more circular shape. However, generally opposing sides of the hand holder 102 may also be flexed inward to exaggerate the elliptical shape. This allows the device to be used with most body types. For example, with a bed-ridden obese patient, a medical care provider may squeeze into a narrow elliptical shape so the device can be positioned between the patient's legs and against the perineum.

Figure 2A:
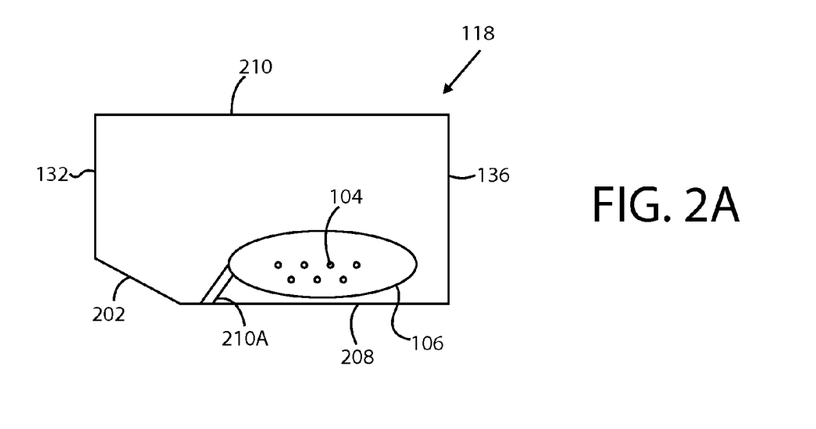
FIGS. 2A-C illustrate alternative embodiments for an inner bag attached inside disposable urine catching devices of FIGS. 1A-B.
Figure 2B:
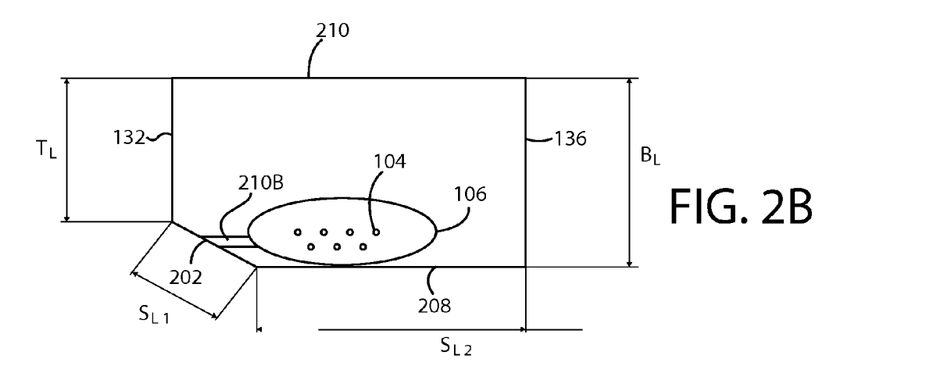
Figure 2C:
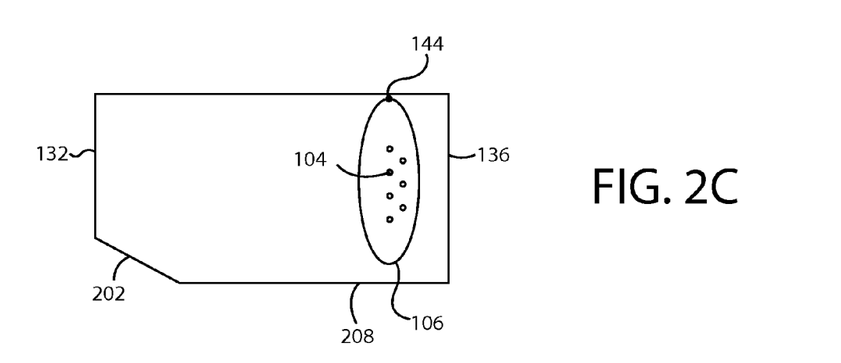

FIGS. 2A-2C are simplified side views of disposable urine catching devices 100A-B in some embodiments. FIG. 2A shows that urine containment bag 118 has a substantially rectangular shape having a formed angle 202 at a "missing" corner. Urine containment bag 118 has an open end 132, a closed end 136 opposite to open end 132, a bottom side 208 and a top side 210 that are between open end 132 and closed end 136. Urine containment bag 118 also has an angled side 202 connecting a bottom of open end 132 and an end of bottom side 208. Angled side 202 has an acute angle from side 208 or direction 230 of fluid flow into urine containment bag 118 and helps guide or direct urine flow into urine containment bag 118.

FIG. 2A also illustrates one configuration of attachment of inner bag 106 to urine containment bag 118. Inner bag 106 contains absorbent powders 104, and may be attached to side 208 of urine containment bag 118 by attachment 210A that forms an acute angle from side 208.

FIG. 2B illustrates another configuration of attachment of inner bag 106 to urine containment bag 118. Inner bag 106 containing absorbent powders 104 is attached to angled side 202 of urine containment bag 118 by attachment 210B, which is substantially parallel to side 208 of urine containment bag 118. Inner bag 106 may be attached to urine containment bag 118 by heat sealing or adhesive bonding. Attachments 210A and 210B are properly positioned to allow expansion of absorbent powers 104 and urine. Inner bag 106 may also be positioned near closed end 136 of urine containment bag 118, as illustrated in FIG. 2C. The number of attachment points or positions may vary.

Urine containment bag 118 may have the following dimensions. For example, open end 132 of urine containment bag 118 has a length $T_L$ of 4 inches, side 202 has an angle of about 30 degrees from the open end 132, and a length $S_{L1}$ of 3 inches, side 208 has a length $S_{L2}$ of 7 inches, and closed end 136 of urine containment bag 118 has a length $B_L$ of 6 inches. It will be appreciated by those skilled in the art that all the dimensions including angle and lengths may vary for the urine catching device.

Inner bag 106 retains absorbent powders 104 to prevent spill and leakage during shipping after the devices 100A-B and 100D are used. Inner bag 106 may be made of a permeable material, such as woven or knit nylon. Absorbent powders 104 may be polyacrylate powders. Polyacrylate powders are used to absorb liquid quickly by forming a gel-solid such that inner bag 106 filled with poyacrylate powders expands with inflow of urine. The polyacrylate powders are also used in baby diapers, feminine hygiene products and similar fluid absorbing devices. The polyacrylate powders can absorb about 400 times its density in water. Each pound of the polyacrylate powders absorbs about 40 gallons of water. The rate of absorption depends on the type of fluid absorbed and temperature. In a particular embodiment, about ten to fourteen grams of absorbent powders 104 may be used.

Figure 3A:
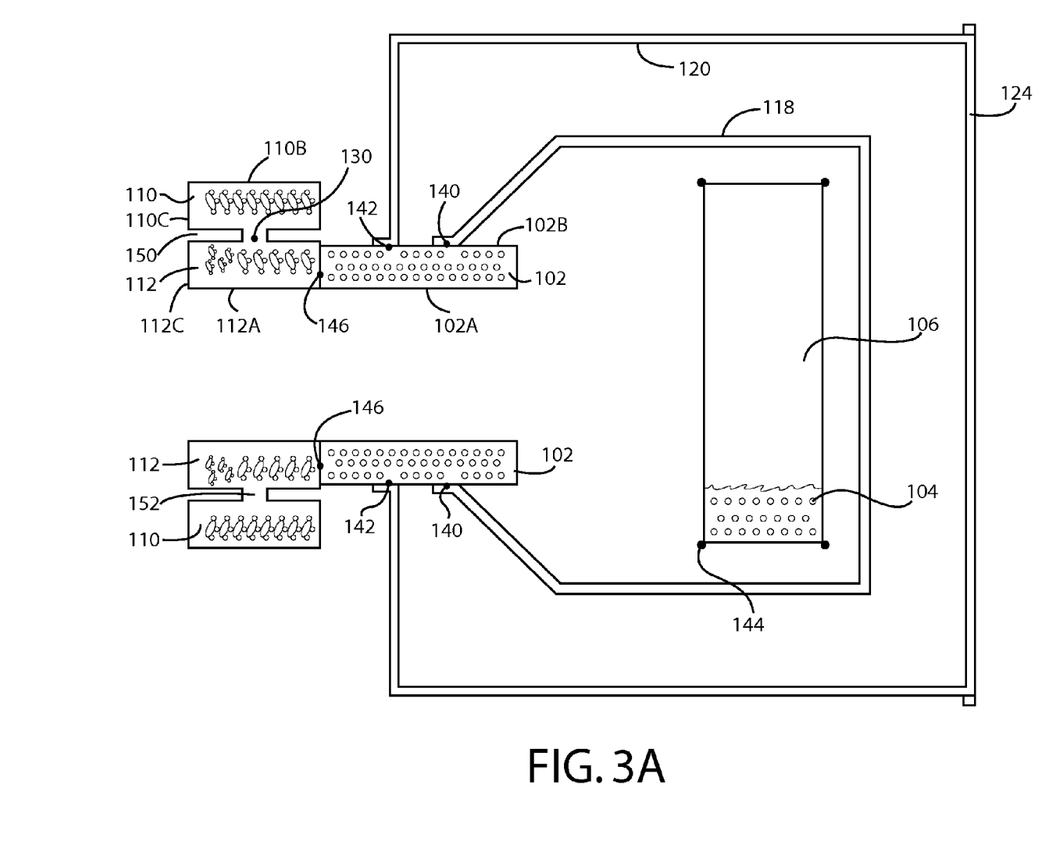
FIG. 3A is a detailed cross sectional view of disposable urine catching device of FIG. 1A in one embodiment.

FIG. 3A is a detailed cross-sectional view of the urine catching device 100A of FIG. 1A in one embodiment. As illustrated in FIG. 3A, hand holder 102 is coupled to a bottom of inner ring 112 through an attachment 146. One method uses double sided acrylic adhesive polyester film. Other adhesives or fusion techniques may be used. Hand holder 102 may be made of a relatively dense structural foam, which is strong to provide firm hand hold for a user. Inner and outer rings 112 and 110 may be made of a relatively less dense foam than hand holder 102 and are more flexible than hand holder 102. The rings are made of an absorbent and flexible material such that the rings conform to a human body contour of any user and provide a close fit to human body and thus minimize fluid leakage. The foam for the hand holder may be a high density closed cell polyethylene foam and the foam for the rings may be a low density hydrophilic polyurethane foam.

Inner ring 112 and outer ring 110 may be formed by cutting a relatively thick structural foam in the middle from both the top surface and bottom surface such that a thin circumferential portion 152 remains intact near the middle of the rings. The circumferential portion 152 helps prevent from liquid leakage between the rings and allows the rings to be offset without fully separating. Separation 150 between the rings allow inner ring and outer ring to have relatively independent end movements or deformation during use. An additional attachment 130 may be added between the inner ring 112 and outer ring 110 to ensure the connection of the two rings during usage. For example, the two rings may be stitched at attachment 130. Adhesive may also be used to reinforce the attachment of the two rings at attachment 130. Additional methods of separating the inner and outer rings may also be used, such as cutting through the entire thickness from top to bottom except for certain areas that act to hold the two rings together.

Outer shield bag 120 is attached to outer surface 102B of hand holder, or tube, 102 at location 142. Urine containment bag 118 is attached to outer surface 102B of hand holder 102 at location 140. Location 142 is closer to the rings than location 140. Locations 142 and 140 could also be at the same point. Attachment at locations 140, 142 and 146 may be achieved with heat sealing or adhesive bonding.

Figure 3B:
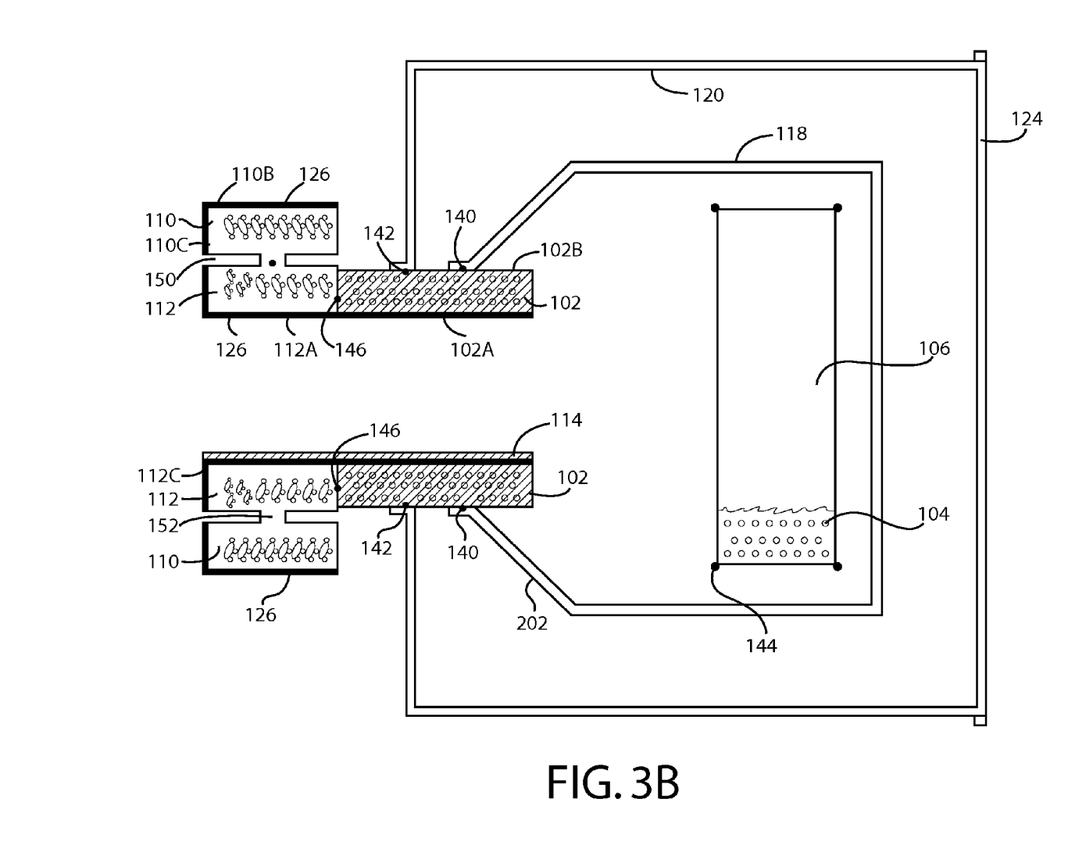
FIG. 3B is a detailed cross sectional view of disposable urine catching device of FIG. 1A in another embodiment.
Figure 3C:
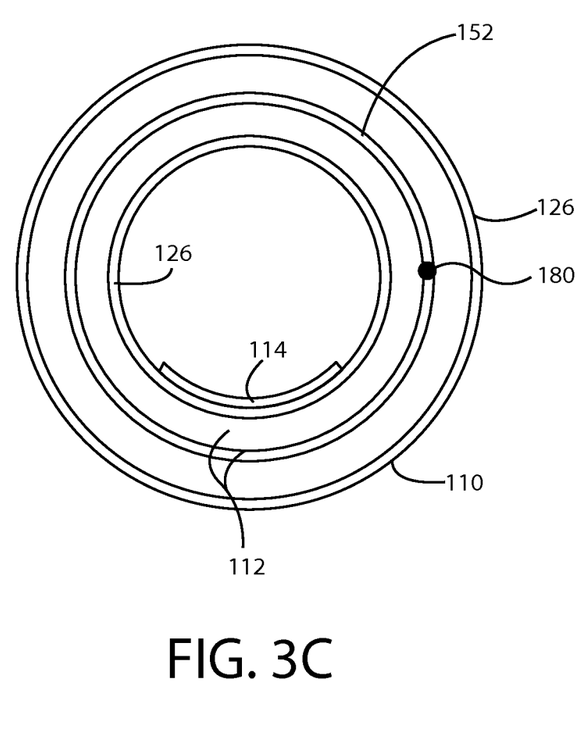
FIG. 3C is a front view of the inner ring and outer ring of FIG. 3B when they are fully opened for usage.

FIG. 3B is a detailed cross-sectional view of the urine catching device 100A in another embodiment. As shown in FIGS. 3B and 3C, an absorbent layer 126 and a waterproof liner 114 may be added inward the inner ring to the embodiment in FIG. 3A. Absorbent layer 126 further enhances absorbance of the rings. Waterproof liner 114 is added to help direct urine to flow into urine containment bag 118.

Absorbent soft fabric 126 wraps on the outer surface 110B and top surface 110C of outer ring 110. Absorbent soft fabric 126 also wraps on inner surface 112A and top surface 112C of inner ring 112 and outer ring 110. Absorbent soft fabric 126 also wraps on inner surface 102A of hand holder 102.

As illustrated in FIGS. 3B and 3C, waterproof liner 114 partially covers the absorbent layer 126 on the inner surface 112A of inner ring 112 and the inner surface 102A of hand holder 102. Circumferential portion 152 remains between inner ring 112 and outer ring 110 to prevent leakage between the two rings and to facilitate offset of the inner ring with respect to the outer ring to assist the user in urging the device into a relatively tight fit with the patient's body. Reinforcement may be optionally added at attachment 130.

Polyethylene foam is a highly elastic, lightweight, and closed cell material. For example, a 0.375 inches thick polyethylene foam may be used to make hand holder 102. Hand holder 102 may be molded in a one-piece configuration or may be formed from a sheet material and heat sealed or adhesive bonded to form a closure with a seam 170 along the angled bottom as illustrated in FIGS. 1C, 1E, and 1F. If heat sealed or bonded, an adhesive tape, such as a polyethylene foam tape with acrylic adhesive on one side of the tape can be used to reinforce the seam. The adhesive tape may be applied either on inner and outer seam surface.

The lateral length for hand holder may be 3 inches. Polyethylene foam is available in a range of densities and colors, and in planks and rolls. Fabrication of polyethylene foam is relatively easy and cost effective. In a particular embodiment, the outer circumference of inner ring 112 may be 10 to 11 inches and the inner circumference of inner ring 112 may be 9 to 10 inches. Outer ring 110 may have an outer circumference of 11 to 12 inches. Soft fabric 126 may be highly absorbent material, such as OASIS SAF®, Super Absorbent Fibers provided by M2 Polymer Technologies, Inc. that are used in feminine hygiene products, or cellulose, among others. Absorbent fabric 126 may be 0.25 inches thick.

Waterproof liner 114 is soft, non-abrasive, waterproof, and suitable for sensitive skin contact. Waterproof liner 114 creates a thin protective seal for the rings and hand holder. Waterproof liner 114 may be a clear single-side adhesive tape, such as 3M Steri-Drape™ Incise Drapes, which are clear adhesive surgical drapes that provide a sterile surface to a wound edge. The single-side adhesive tape is adhered to the absorbent rings such that the non-sticky side contacts the user.

Figure 4A:
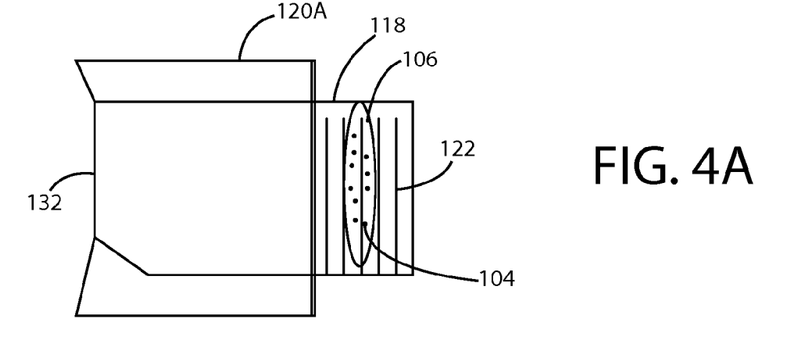
FIGS. 4A-C illustrate different exemplary configurations of the outer shield bag of FIGS. 1A-B.
Figure 4B:
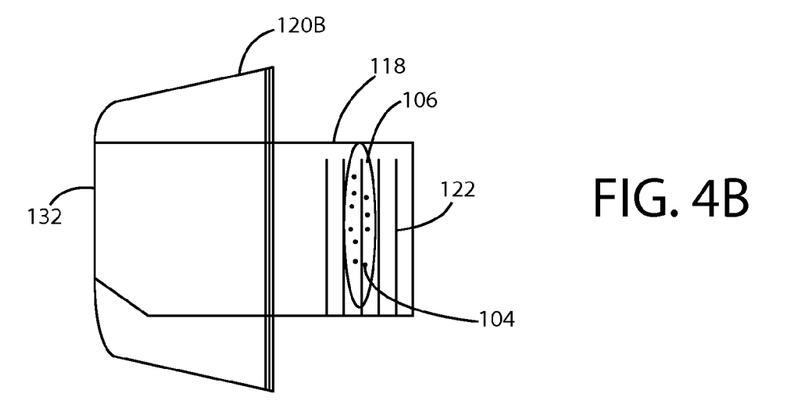
Figure 4C:
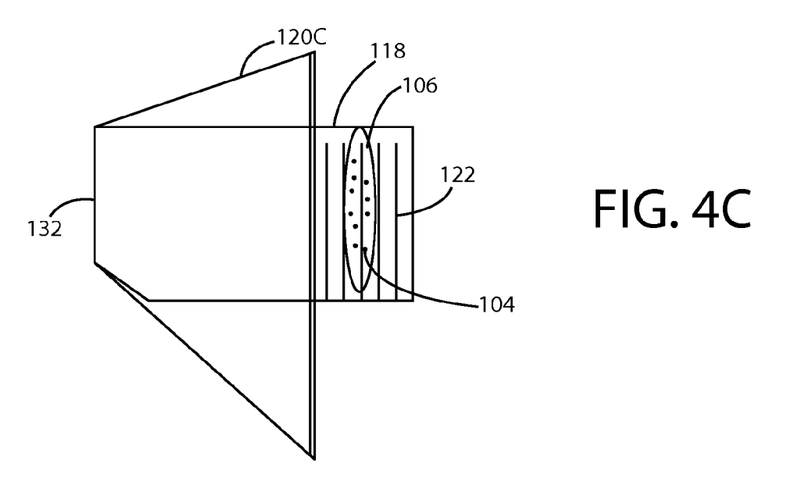

FIGS. 4A-C illustrate different configurations of an outer shield bag attached to inner ring 112 in some embodiments. Outer shield bags 120A, 120B and 120C have different shapes and angles near open end 132. Note that outer shield bag 120B has curved edges close to open end 132. The corners of outer shield bag 120 and urine containment bag 118 may be rounded (not shown).

Outer shield bag 120 may be attached to hand holder 102 by heat sealing, or adhesive bonding, such as adhesive tape. Outer shield bag 120 may be made of polyethylene or any other suitable material. Incremental reading measurements 122 are near the bottom of urine containment bag 118. Outer shield bag 120 with sealable closure 124 serves as hand shield during usage to allow a user's hand to grasp the hand holder 102 in order to properly position the urine containment device on the perineum. The outer shield bag also allows users for easy and clean disposal of liquid. Outer shield bag 120, urine containment bag 118 and inner bag 106 may be transparent or colored.

Figure 5A:
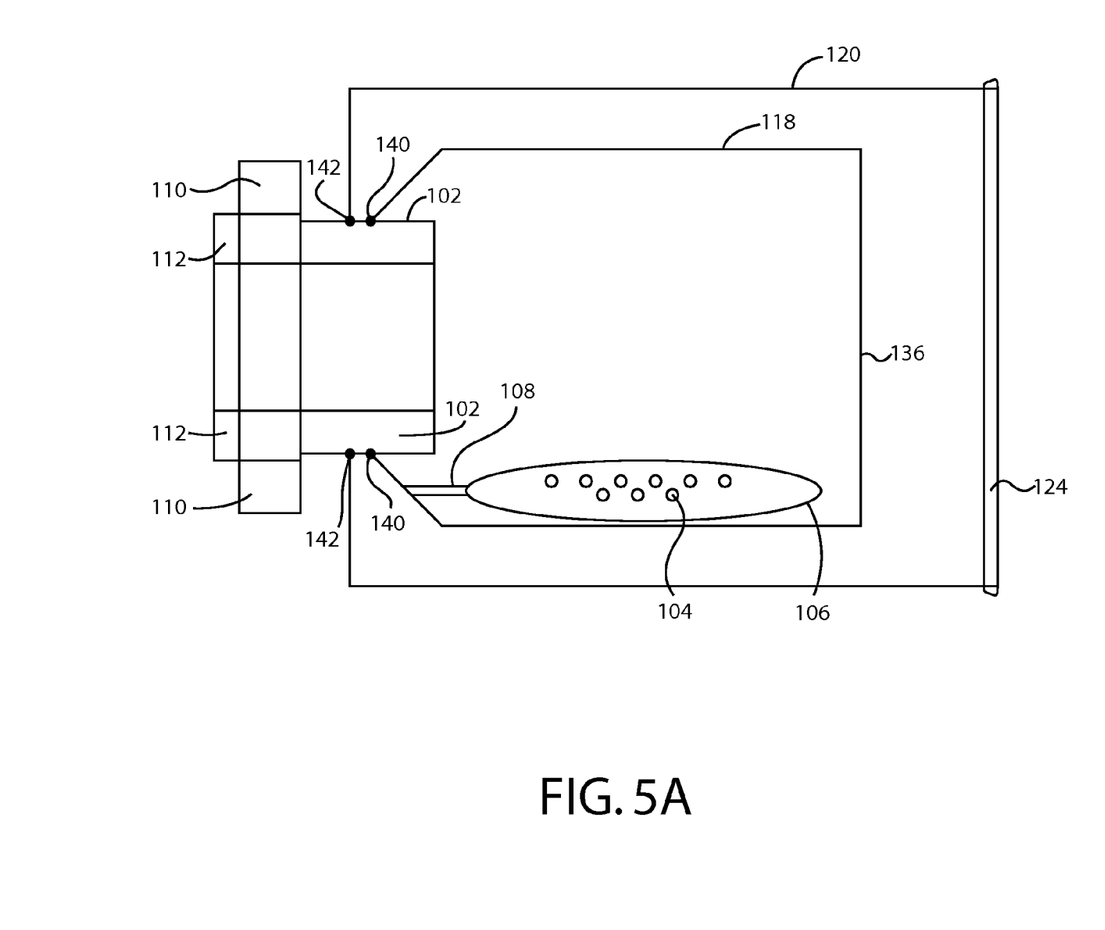
FIGS. 5A-B are alternative embodiments of FIG. 1A with lateral offsets between the inner ring and outer ring.
Figure 5B:
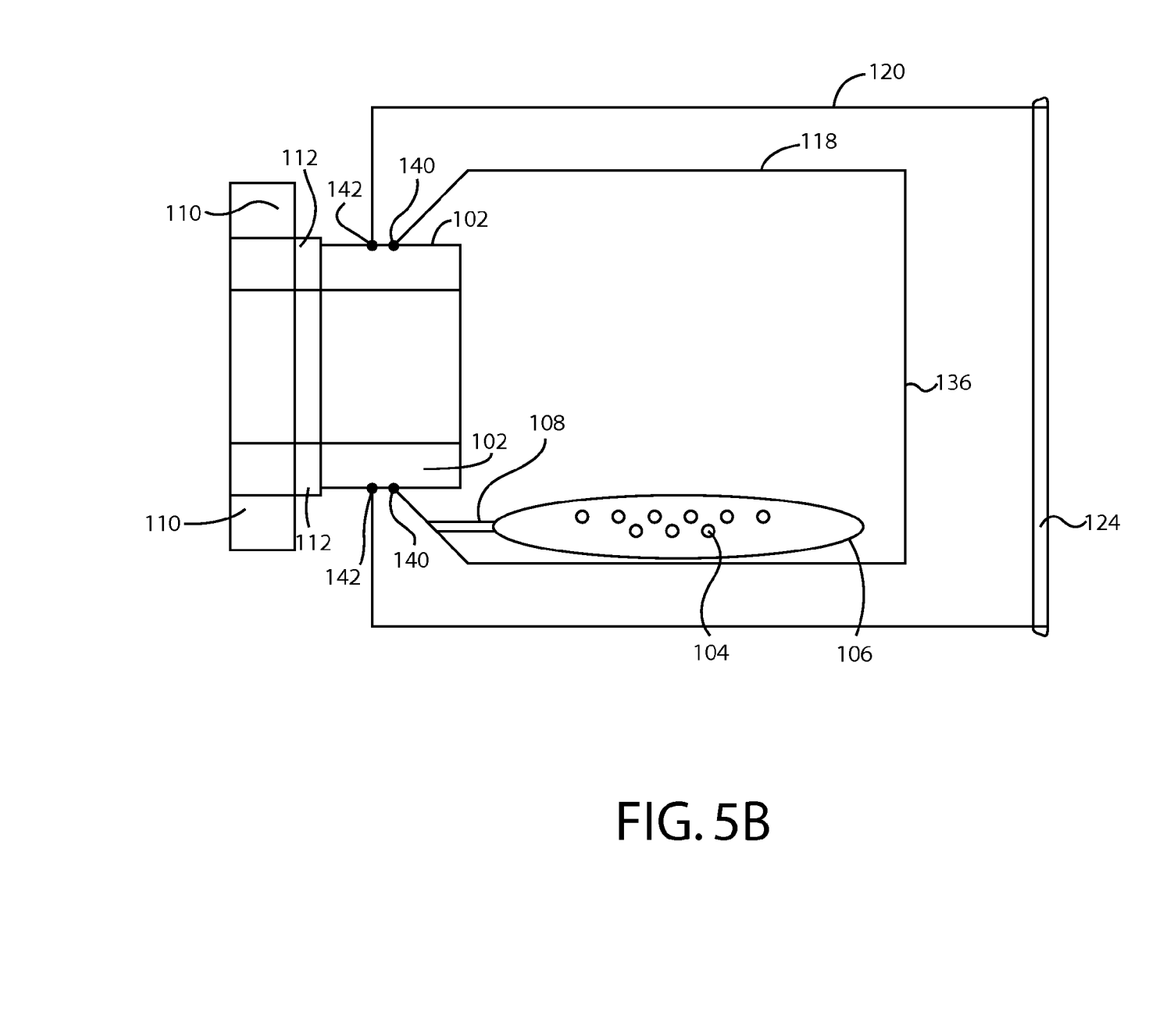

FIGS. 5A-B illustrate different lateral lengths for inner ring 110 and outer ring 112 in some embodiments. The offset between inner ring 112 and outer ring 110 may vary. The top surface of inner ring 112 or the top surface of outer ring 110 or both top surfaces may be placed firmly against the perineum of the person urinating into the device. Urine is directed through opening of inner ring 112 into urine containment bag 118. The absorbent foam of the inner and outer rings and/or the absorbent fabric 126 of the inner and outer rings captures and retains any urine not directed into the bag 118. Moreover, the concentric rings can be deformed with slight pressure to create substantial seal between the top surface of the inner ring and the perineum of the user.

Figure 6:
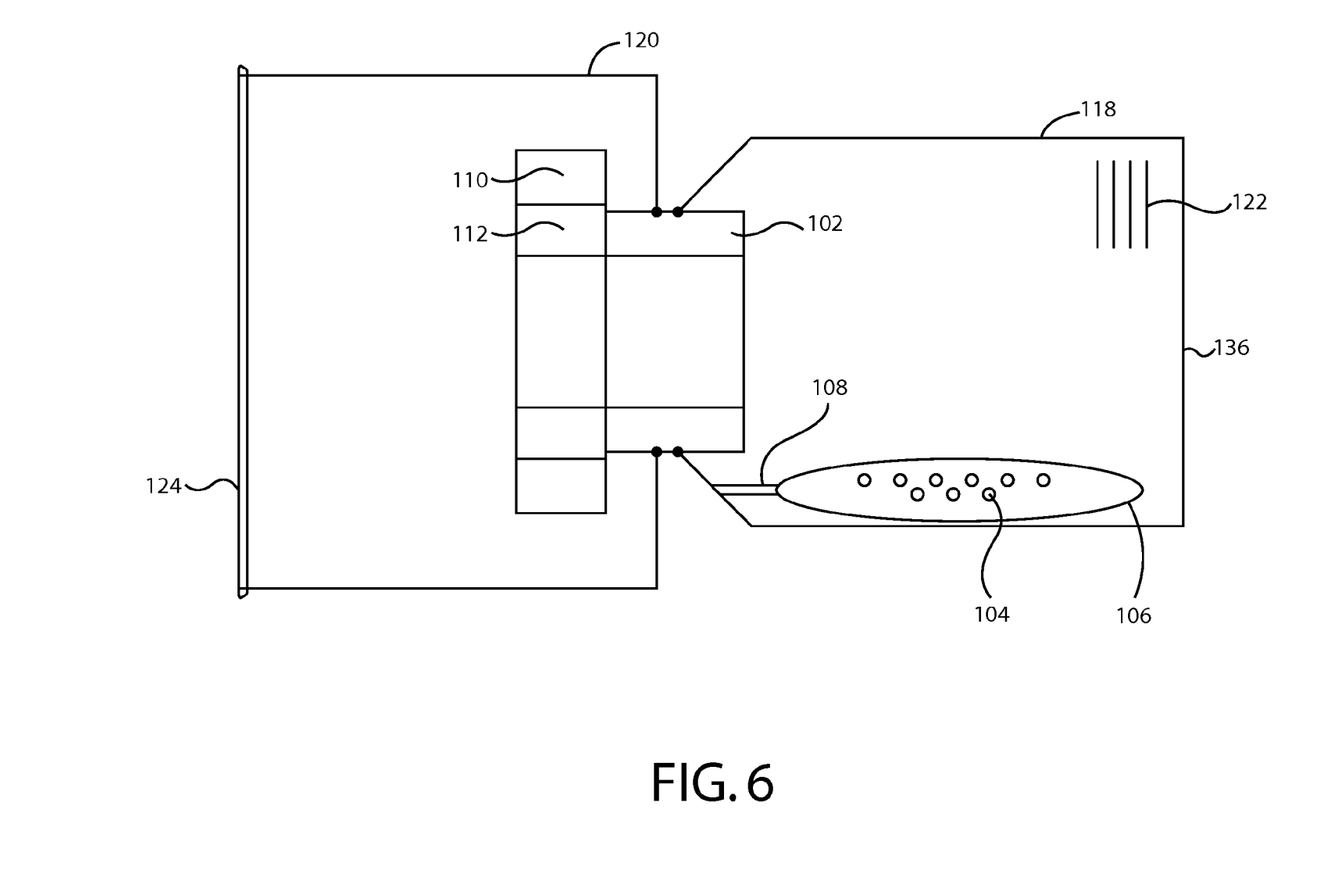
FIG. 6 illustrates that the outer shield bag turns inside out when the devices of FIGS. 1A-B is in use in an embodiment.

To use device 100A, 100B, or 100D, males simply urinate into urine containment bag 118 positioning urine streams through opening of inner ring 112. Where a male patient is being assisted by medical staff, the urine bag can be forced against the perineum with the absorbent rings preventing urine leakage. Absorbent powders 104 within inner bag 106 capture and hold urine thereby limiting the likelihood of spills or leakage. After usage, the rings 112 and 110 and hand holder 102 are sealed by reversing outer shield bag 120 and sealable closure 124 as illustrated in FIG. 6. Sealable closure 124 seals urine containment bag 118 and contact or top surfaces of inner ring 112 and outer ring 110. The device can be used by both male and females. The device is also intended for use in a nursing home or hospital setting where a patient may use the device alone. The patient may also use the device with the assistance of a health care provider. The device is particularly well-suited for use by bed ridden patients, because it substantially decreases the likelihood of spillage and leaking which is common with bed pans or other devices. The device may have many other non-medical applications such as use when traveling. The devices are lightweight, easy and inexpensive to manufacture and can be safely and easily disposed.

One of the benefits of the urine catching device is that patients may urinate at various supine or recumbent body positions. Additional benefits include urine spill prevention and easy and safe disposal of the device after usage.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A sanitary disposable unisex urinal device comprising:
    an inner ring having a top surface an opposing bottom surface and an outer surface extending from the top surface to the bottom surface thereof;
    an outer ring having a top surface and an opposing bottom surface, the outer ring being substantially concentric with the inner ring, wherein the inner ring is connected to the outer ring along a circumference located between the top surface and the bottom surface of each ring;

an outer shield bag having an open end and closable end;
a tube coupled to the bottom surface of the inner ring at a first end of the tube, the first end of the tube having an opening configured to match to the inner ring;
a urine containment bag having an open end; and
wherein the tube is secured within the open end of the urine containment bag.

2. The device of claim 1 further wherein the outer shield bag is attached to the outer surface of the tube at the same position as the urine containment bag.

3. The device of claim 2 wherein the inner and outer rings comprise an absorbent foam material.

4. The device of claim 2 wherein the tube comprises a plastic material.

5. A method of utilizing the sanitary disposable unisex urine device of claim 2, comprising the steps of:
   opening the outer shield bag and retracting the outer shield bag over the tube;
   positioning the top surface of the inner and outer rings against the body of a user;
   directing urine through the rings and the tube into the urine containment bag; and
   reversing the outer shield bag to seal the urine containment bag.

6. A sanitary disposable unisex urinal device comprising:
an inner ring having a top surface an opposing bottom surface and an outer surface extending from the top surface to the bottom surface thereof, wherein the inner ring comprises an absorbent foam material;
an outer ring having a top surface and an opposing bottom surface, the outer ring being substantially concentric with the inner ring, wherein the inner ring is connected to the outer ring along a circumference located between the top surface and the bottom surface of each ring;
a tube coupled to the bottom surface of the inner ring at a first end of the tube, the first end of the tube having an opening configured to match to the inner ring;
a urine containment bag having an open end; and
wherein the tube is secured within the open end of the urine containment bag.

7. The device of claim 6 further comprising an outer shield bag attached to the outer surface of the tube at the same position as the urine containment bag.

\* \* \* \* \*